(12) United States Patent
DeToro et al.

(10) Patent No.: US 6,350,246 B1
(45) Date of Patent: Feb. 26, 2002

(54) ANKLE AND FOOT THERAPEUTIC DEVICE

(75) Inventors: William DeToro, Poland; Brian Perala, Geneva, both of OH (US)

(73) Assignee: Anatomical Concepts, Inc., Youngstown, OH (US)

( * ) Notice: Subject to any disclaimer, the term of this patent is extended or adjusted under 35 U.S.C. 154(b) by 0 days.

(21) Appl. No.: 09/511,285

(22) Filed: Feb. 23, 2000

(51) Int. Cl.[7] .............................. A61F 5/00; A61F 5/37
(52) U.S. Cl. ........................ 602/27; 602/16; 128/882
(58) Field of Search .......................... 602/5, 16, 23, 602/27, 60–62, 65; 128/882; 623/39, 47, 52; 2/22

(56) References Cited

U.S. PATENT DOCUMENTS

| | | | | |
|---|---|---|---|---|
| 1,383,928 A | * | 7/1921 | Gassette | 602/16 |
| 3,086,521 A | * | 4/1963 | Desai et al. | 128/80 |
| 3,732,862 A | * | 5/1973 | Golia | 128/80 E |
| 4,771,768 A | | 9/1988 | Crispin | |
| 5,014,690 A | | 5/1991 | Hepburn et al. | |
| 5,224,925 A | * | 7/1993 | Varn | 602/28 |
| 5,520,627 A | * | 5/1996 | Malewicz | 602/26 |
| 5,593,383 A | * | 1/1997 | DeToro | 602/27 |
| 5,611,773 A | | 3/1997 | Nash et al. | |
| 5,797,865 A | | 8/1998 | McDavid, III | |
| 5,830,166 A | * | 11/1998 | Klopf | 602/16 |
| 5,865,778 A | | 2/1999 | Johnson | |
| 5,873,847 A | * | 2/1999 | Bennett et al. | 602/16 |
| 5,902,259 A | * | 5/1999 | Wilkerson | 602/27 |
| 5,908,398 A | | 6/1999 | DeToro | |
| 6,203,511 B1 | * | 3/2001 | Johnson et al. | 602/16 |

* cited by examiner

*Primary Examiner*—Denise Pothier
(74) *Attorney, Agent, or Firm*—Harpman & Harpman

(57) ABSTRACT

An ankle and foot therapeutic device for use in supporting a patient's foot and leg and selectively immobilizing the patient's ankle. The brace is of a multiple part configuration having a heel portion, leg portion and foot portion. The leg portion and foot portion being interconnected by a range of motion assembly. The range of motion assembly having a pivot point for adjustable plantar and dorsi flexion by the patient's foot. The heel portion having a configuration to provide a space with the patient's heel.

10 Claims, 5 Drawing Sheets

ANKLE AND FOOT THERAPEUTIC DEVICE

BACKGROUND OF THE INVENTION

1. Technical Field

This device relates to therapeutic ankle and foot brace devices that are removably secured to a patient's foot and leg. Such devices are used to firmly support a patient's leg, foot, and ankle of the patient for therapeutic purposes.

2. Description of Prior Art

Prior art devices of this type are directed to a variety of leg and foot brace configurations to stabilize the foot having articulated joints to provide for a range of motion between the foot portion and the leg portion as seen in U.S. Pat. Nos. 4,771,768, 5,014,690, 5,611,773, 5,797,865 and 5,865,778.

In U.S. Pat. No. 4,771,768 a controlled motion ankle fracture walker is disclosed having a leg support interconnected to a foot support by a pair of pivotable rigid, lateral and medial uprights which allow for dorsi flexion or plantar flexion by the double action intersecting joints.

U.S. Pat. No. 5,014,690, claims an adjustable splint leg having a pair of spaced upper leg engagement struts pivotally connected to a pair of lower struts being spring bias with a cam surface defining a lower strut pivot point.

U.S. Pat. No. 5,611,773 is directed to an ankle pivot cap for the capture of a dorsi flexion and plantar flexion detent pins.

U.S. Pat. No. 5,797,865 has a lightweight ankle restraint made of plastic material with a pair of splint plates pivotally connected to struts of a foot engagement stirrup.

In U.S. Pat. No. 5,865,778 foot wear with integrated ankle support is disclosed wherein a resilient pivoting ankle brace has a malleable upper stirrup and a lower stirrup interconnected by an adjustment range of motion joint.

DeToro's own U.S. Pat. No. 5,908,398 is directed to an adjustable ankle and foot orthosis brace having an upper control leg support portion and a foot portion interconnected by an intermediate adjustable hinge assembly.

SUMMARY OF THE INVENTION

Applicant's device is directed to an ankle and foot orthosis that protects the patient's heel from pressure. The device having a leg portion and a foot portion with a range of motion assembly interconnecting there between. Fabric foot and leg securing straps are used to attach the leg and foot portion to the patient. This invention provides for limited plantar and dorsi flexion of the foot portion with an adjustable motion range stop in the range of motion assembly in spaced relation to leg and foot support portions.

DESCRIPTION OF THE PREFERRED EMBODIMENT

Figure 1:
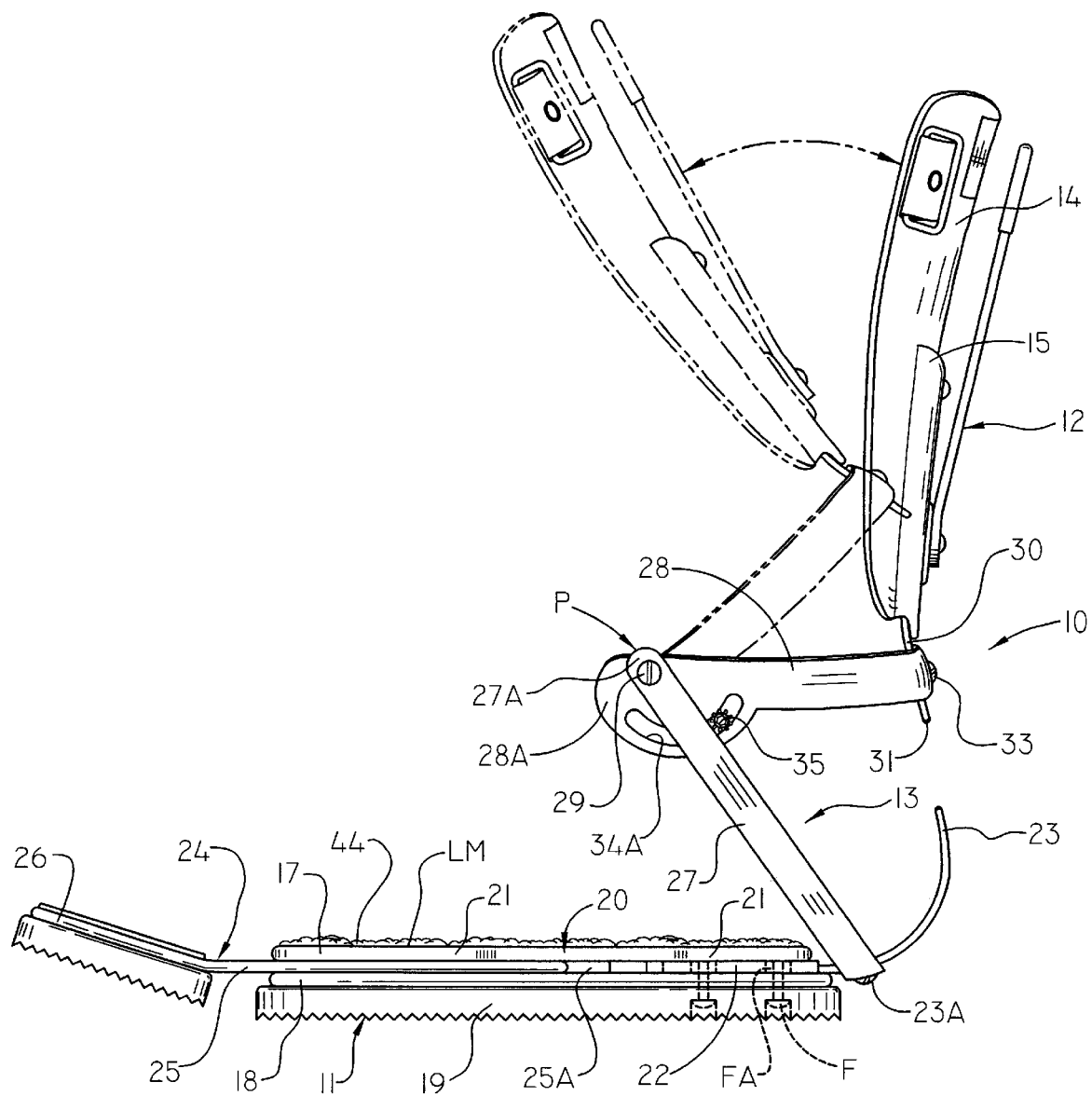
FIG. 1 is a side elevational view of the range of motion orthotic brace with leg and foot securing fabric attachment elements removed for illustration purposes.
Figure 2:
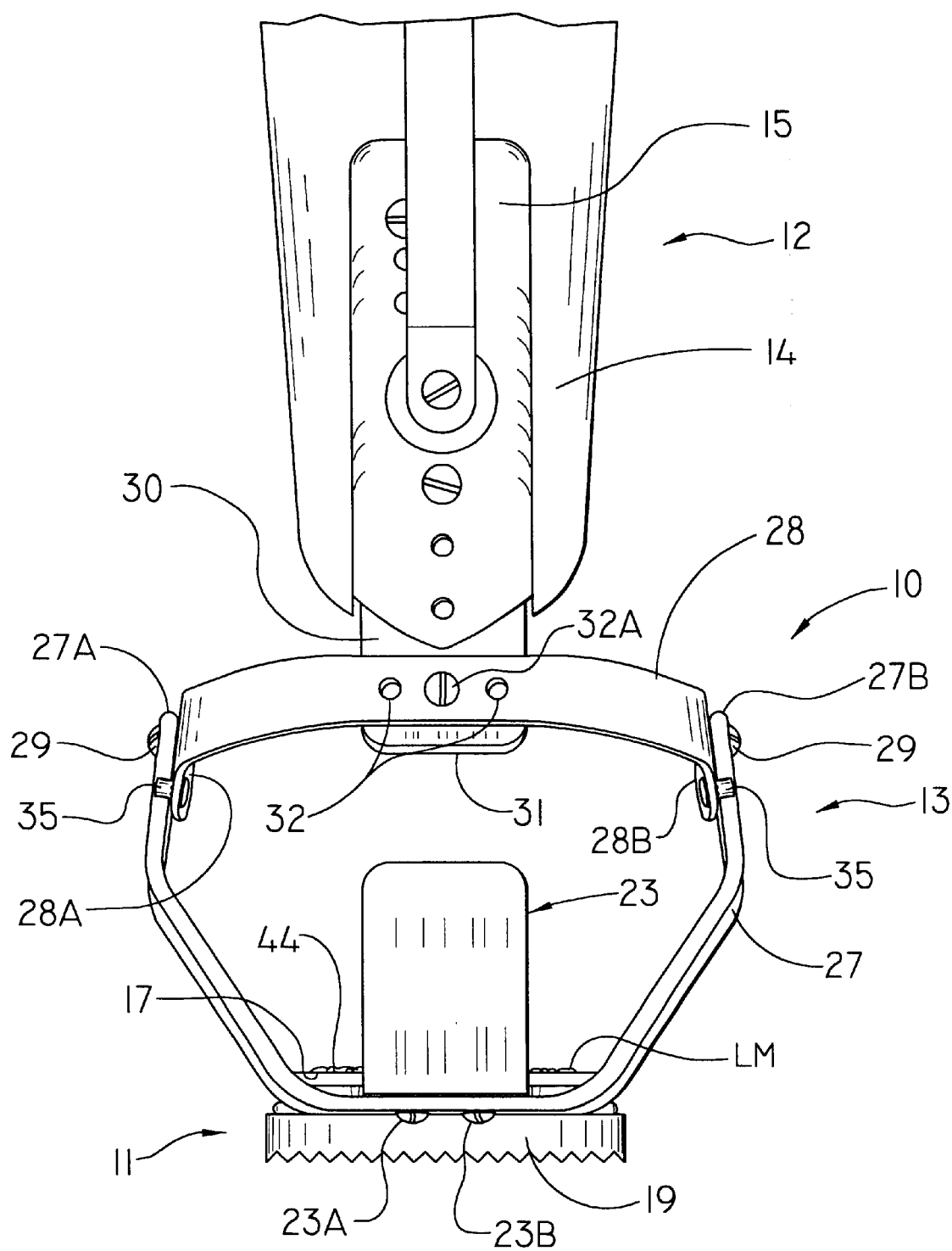
FIG. 2 is an enlarged partial rear elevational view of the leg and foot portions with interconnecting range of motion assembly in the non-flex position.
Figure 3:
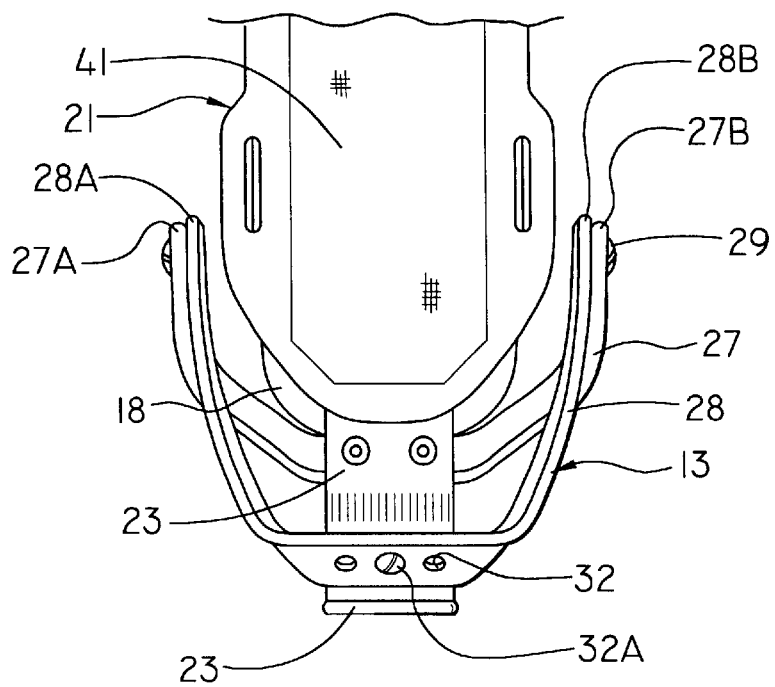
FIG. 3 is a partial top plan view of the range of motion assembly interconnecting the leg and foot portions of the brace of the invention.
Figure 4:
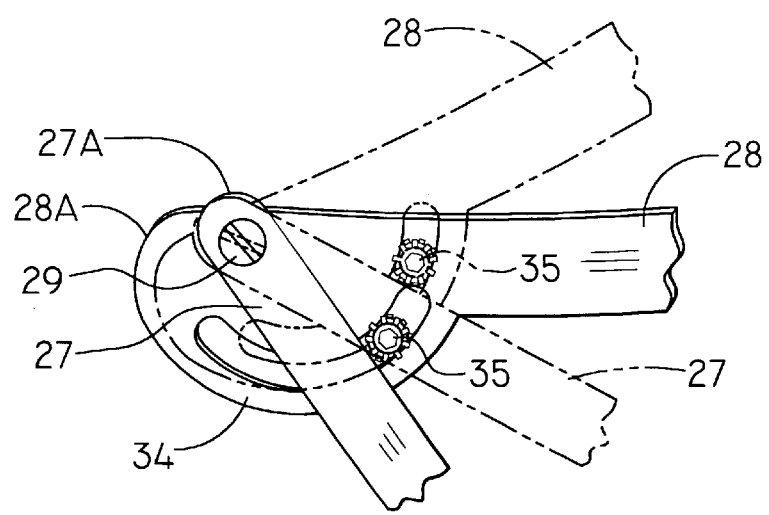
FIG. 4 is an enlarged side elevational view of the range of motion assembly positioned at various angles.
Figure 5:
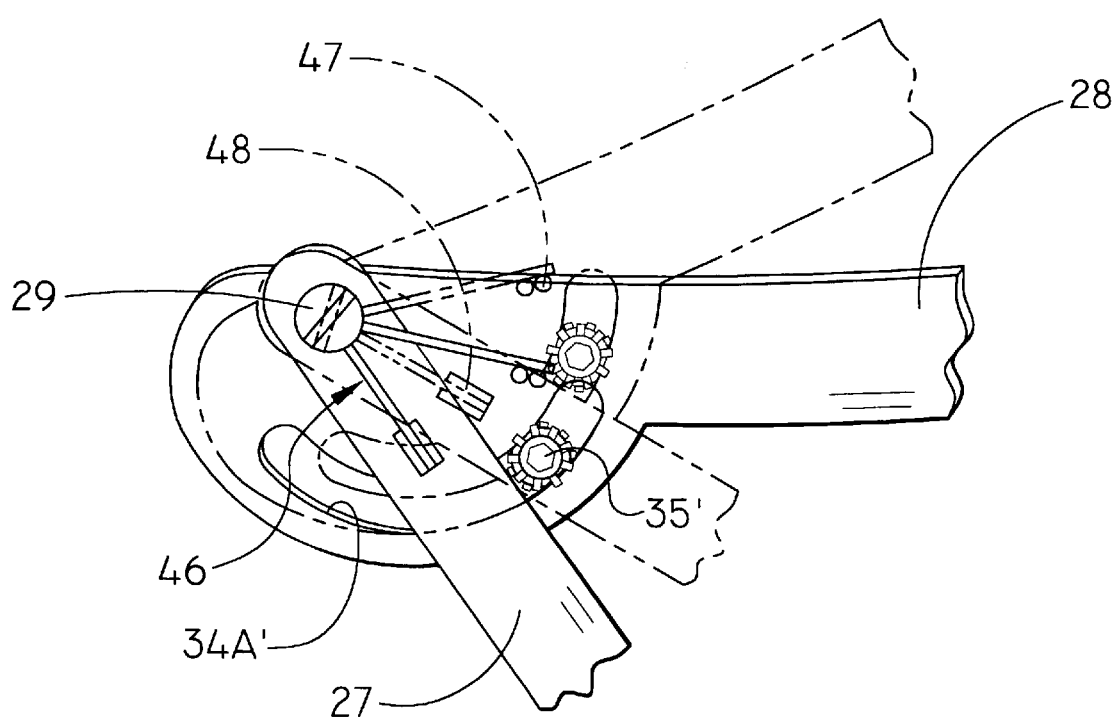
FIG. 5 is an enlarged side elevational view of an alternate form of the invention having a resilient element within the range of motion assembly.
Figure 6:
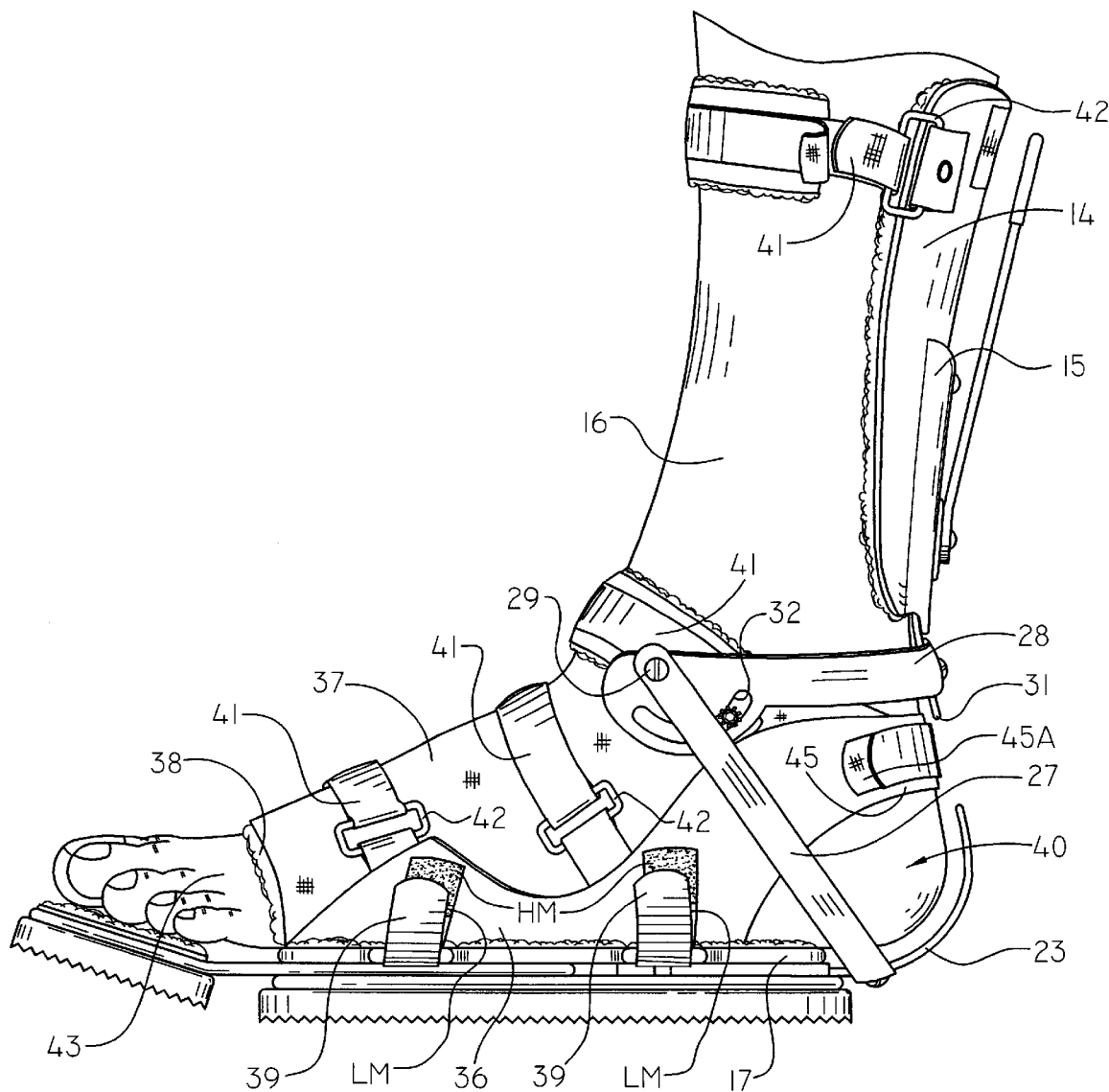
FIG. 6 is a side elevational view of the orthotic brace having range of motion with the leg and foot securing fabric shown.

Referring now to FIGS. 2–6 of the drawings, the adjustable range of motion orthotic ankle and foot brace 10 of the invention can be seen having a foot portion 11, a leg portion 12 and an interconnecting range of motion assembly 13 there between. The leg portion 12 has an enlarged transversely contoured leg support 14 with a recess channel 15 formed therein. Typically, the leg portion 12 is made of synthetic plastic resin and can be molded or prepared to the desired contours required for engagement with a patient's leg 16 as best seen in FIG. 6 of the drawings. The foot portion 11 has a contoured footpad 17 connected to a generally rectangular attachment brace 18. A resilient walking pad 19 is secured to the attachment brace 18. The foot pad 17 has an area of reduced transverse dimension at 20 with respective pairs of longitudinally spaced apertured tabs 21 extending therefrom as best seen in FIG. 3 of the drawings. A mounting pocket 22 extends inwardly from the bottom of the footpad 17 for engagement with a heel portion 23 that extends therefrom as best seen in FIGS. 1, 2 and 6 of the drawings. The heel portion 23 having a curved configuration to provide a space with the patient's heel.

A toe support extension member 24 adjustably extends from the footpad 17 opposite the hereinbefore-described mounting pocket 22. The toe support extension member 24 has a flat base area 25 with an angularly offset end portion 26.

The range of motion assembly 13 has a bifurcated lower ankle support member 27 that is rigidly secured to the heel portion 23 adjacent the attachment base 18 by point of attachment fasteners 23A and 23B as shown in FIG. 2. The bifurcated lower ankle support member 27 extends upwardly and diagonally from its heel attachment point as best seen in FIGS. 1 and 6 of the drawings. A bifurcated upper ankle support member 28 is pivotally connected at its apertured free ends 28A and 28B to respective apertured free ends 27A and 27B of the lower ankle support member 27 defining a pivot point P with pivot fastener pins 29 interconnecting same. The upper ankle support member 28 is in turn secured to a leg support element 30 extending from within the recess channel 15 on the leg portion 12. The leg support element 30 is of an elongated transversely flat bar configuration having mounting apertures inwardly of its free end at 31 aligned for inner engagement with mounting apertures 32 within the upper ankle support member 28 by fasteners 32A as best seen in FIGS. 2 and 3 of the drawings. This arrangement allows for adjustment of the leg portion 12 relative the upper ankle support member 28.

The upper ankle support member 28 has areas of increased transverse dimension at its respective free ends 28A and 28B which define range of motion plates 34 having arcuate slots at 34A and 34B therein. Stop engagement pins 35 are adjustably secured through the slots 34A and 34B respectively so as to provide for incremental selective adjustment of the travel path of the leg portion 12 by engagement with support member 27 as illustrated in broken lines in FIGS. 1 and 4 of the drawings. It will be evident that by establishing a pivot point P inwardly from the heel portion 23 and substantially lateral to the patient's ankle while maintaining points of attachment 23A and 23B of the lower ankle support member 27 to the heel portion 23 and the points of attachment 32 of the upper ankle support member 28 to the leg support element 30 extending from the recess channel 15 of the leg portion 12 that the preferred and selected range of dorsi and plantar flexion can be achieved while providing patient heel protection in both the ambulatory and rest venues.

Referring now to FIG. 6 of the drawings, a fabric foot securing enclosure is illustrated having a durable mounting base portion 36 securing a fabric sleeve 37 that is lined with a soft synthetic fur like material 38. The durable mounting base 36 provides a reinforced contoured mounting surface for securing a plurality of fastening straps 39 that are used to removably secure the foot engagement enclosure to the footpad 17. The durable mounting base 36 and overlapping fabric sleeve 37 define a cutout portion 40 at the heel. Secondary straps 41 extend from the fabric sleeve 37 and the durable mounting base 36 for registered engagement through respective buckles 42 to secure the fabric sleeve 37 about the patient's foot 43. Releasable securing hook material HM and loop material LM collectively referred to as releasable securing material such as Velcro is used on the fastening straps 39 and secondary straps 41 so that they can be secured to themselves after engagement through respective buckles 42 and apertured tabs 21 as will be well understood by those skilled in the art.

It will be seen that the releasable securing loop material LM is respectively positioned on the footpad 17 at 44. The releasable securing loop material LM is aligned with releasable securing hook material HM on the durable mounting base 36 between the multiple fastening straps 39.

It will be evident from the above description that the fastening straps 39 provide the means for positioning and securing the foot securing enclosure to the rigid footpad 17 by engagement through the respective aperture tabs 21. Once the fabric sleeve 37 has been releasably secured to the foot pad 17, it is gathered about and around the patient's heel 40 and secured by overlapping portions 45 using the same releasable securing material LM and HM on heel strips 45A respectively, as best seen in FIG. 6 of the drawings.

Referring now to FIG. 5 of the drawings, an alternate form of the invention can be seen wherein the interconnecting range of motion assembly 13 has been modified at its interengaging pivot points P. A return spring element 46 is secured adjacent to the lower ankle support member's free ends 27A and 27B through an opening 48 and extends around the pivot pin 29. The return spring element 46 resiliently engages the upper ankle support element 28 via a pair of engagement pins 47 extending therefrom to impart spring resistance thereto providing dorsi assist as required.

The alternate form of the invention will also adjustably limit dorsi and plantar flexion movement by use of a stop engagement pin 35' adjustably positioned within an arcuate slot 34A' and 34B' in the upper ankle support element's free ends as hereinbefore described.

It will thus be seen that a new and novel therapeutic ankle and foot orthotic brace has been illustrated and described and it will be apparent to those skilled in the art that various changes and modifications may be made without departing from the spirit of the invention.

We claim:

1. A therapeutic ankle and foot device for a patient, the device comprising: a leg portion, a foot portion and a heel portion, said foot portion being at an angle to said leg portion;

an interconnecting range of motion assembly being integral with one end of said leg portion, said interconnecting range of motion assembly having an upper ankle support member and a lower ankle support member, said upper and lower ankle support members being pivotally connected to one another at a pivot point being lateral to a patient's ankle during use, said ankle support member being integral with and extending upwardly and diagonally from said heel portion, said range of motion assembly having an apertured motion plate with an adjustable stop attached thereto for selective engagement between said lower ankle support member and said upper ankle support member, said apertured motion plate having an arcuate aperture; and said heel portion having a configuration to provide a space between the patient's heel and said heel portion to prevent the application of pressure to the patient's heel, and said heel portion being attached to said foot portion wherein the pivot is inwardly from said heel portion and substantially lateral to the patient's ankle during use such that the range of dorsi and plantar flexion between said leg portion and foot portion may be freely adjusted with the interconnecting range of motion assembly.

2. The therapeutic ankle and foot device as set forth in claim 1, wherein said interconnecting range of motion assembly has a return spring to resiliently engage the upper ankle support member and the lower ankle support member.

3. The therapeutic ankle and foot device as set forth in claim 1, wherein said lower ankle support member is connected to an end of the heel portion adjacent to said foot portion.

4. The therapeutic ankle and foot device as set forth in claim 1, wherein said upper and lower ankle support members are pivotally connected to one another at two pivot points, each pivot point being on opposite sides of and lateral to the patient's ankle during use.

5. The therapeutic ankle and foot device as set forth in claim 1, wherein said adjustable stop attached to said apertured motion plate comprises an engagement pin.

6. A therapeutic ankle and foot device for a patient, the device comprising: a leg portion, a foot portion, a heel portion and range of motion assembly, said foot portion being at adjustable angles to said leg portion;

said range of motion assembly having an upper ankle support member and a lower ankle support member, said upper and lower ankle support members being interconnected to one another at a pivot point, said lower ankle support member being integral with and extending upwardly and diagonally from said heel portion, said range of motion assembly having an apertured motion plate with an adjustable stop extending therefrom for selective engagement, said apertured motion plate having an arcuate aperture and said range of motion assembly further comprising a spring element between said upper and lower ankle support members imparting dorsi flexion force to said foot portion; and said heel portion being curved and extending from said foot portion to provide a space between a patient's heel and said heel portion wherein the pivot point is inwardly from said heel portion and substantially lateral to the patient's ankle during use such that the range of dorsi and plantar flexion between said leg portion and said foot portion may be freely adjusted with said range of motion assembly.

7. The therapeutic ankle and foot device as set forth in claim 6, wherein said lower ankle support member is secured to said heel portion adjacent to said foot portion.

8. The therapeutic ankle and foot device as set forth in claim 6, wherein said upper ankle support member is secured to said leg portion in spaced relation to said heel portion.

9. The therapeutic ankle and foot device as set forth in claim 6, wherein said adjustable stop attached to said motion plate comprises an engagement pin.

10. The therapeutic ankle and foot device as set forth in claim 6, wherein said adjustable stop selectively engages said upper ankle support member, the adjustable stop comprising a selectively positionable engagement pin attached to said range of motion plate.

* * * * *